US007541556B2

(12) United States Patent
Canepa

(10) Patent No.: US 7,541,556 B2
(45) Date of Patent: Jun. 2, 2009

(54) APPARATUS FOR CHECKING THE QUALITY OF PREFORMS EACH HAVING A BODY MADE OF PLASTICS MATERIAL

(75) Inventor: Enzo Canepa, Chiavari (IT)

(73) Assignee: M & G Polymers USA, LLC, Apple Grove, WV (US)

( * ) Notice: Subject to any disclaimer, the term of this patent is extended or adjusted under 35 U.S.C. 154(b) by 214 days.

(21) Appl. No.: 10/556,766

(22) PCT Filed: May 21, 2004

(86) PCT No.: PCT/EP2004/005481

§ 371 (c)(1),
(2), (4) Date: Nov. 16, 2005

(87) PCT Pub. No.: WO2004/103583

PCT Pub. Date: Dec. 2, 2004

(65) Prior Publication Data

US 2006/0219609 A1    Oct. 5, 2006

(30) Foreign Application Priority Data

May 22, 2003  (EP) .................................. 03425330

(51) Int. Cl.
*B07C 5/00* (2006.01)
(52) U.S. Cl. ...................................... 209/524; 209/591
(58) Field of Classification Search ......... 209/522–524, 209/526, 576, 591, 905, 919; 73/45.2
See application file for complete search history.

(56) References Cited

U.S. PATENT DOCUMENTS

| 725,589 | A | * | 4/1903 | Rehfuss ....................... 73/45.3 |
| 2,432,871 | A | * | 12/1947 | Fedorchak et al. ........... 73/45.3 |
| 3,495,441 | A | * | 2/1970 | Laub ........................... 73/45.2 |
| 5,571,949 | A | | 11/1996 | MacLaughlin et al. |
| 5,591,899 | A | * | 1/1997 | Griesbeck ..................... 73/41 |

(Continued)

FOREIGN PATENT DOCUMENTS

JP    11-100119    4/1999

(Continued)

*Primary Examiner*—Patrick H Mackey
*Assistant Examiner*—Mark Hageman
(74) *Attorney, Agent, or Firm*—Edwin A. Sisson, Attorney at Law, LLC

(57) ABSTRACT

The apparatus is intended for performing quality checks on preforms (10) each having a body made of plastics material having an internal cavity (12) communicating with the exterior through an end opening (14) of the body. The apparatus comprises: a conveyor device (20) for transporting the preforms (10) along a predetermined path, an optical device (22) disposed along the path and suitable for forming an image of each of the preforms (10), a pneumatic device (24) disposed along the path and suitable for putting the internal cavity (12) of each of the preforms (10) under partial vacuum for a predetermined period of time, an electronic control unit (28) suitable for comparing the images of the preforms (10) with a standard reference image and/or for checking whether the value of the partial vacuum remains unchanged during the said period of time, and a selector device (26) disposed along the path and capable of separating the preforms (10) on the basis of the result of the comparison and/or checking operations performed by the control unit (28).

4 Claims, 4 Drawing Sheets

U.S. PATENT DOCUMENTS 5,719,679 A * 2/1998 Shimizu et al. ............. 356/428
6,050,134 A * 4/2000 Strand ........................ 73/49.2
6,473,169 B1 10/2002 Dawley et al.
6,557,695 B2 * 5/2003 Gerber et al. ............ 198/473.1

FOREIGN PATENT DOCUMENTS

WO   WO 01/25761   4/2001

* cited by examiner

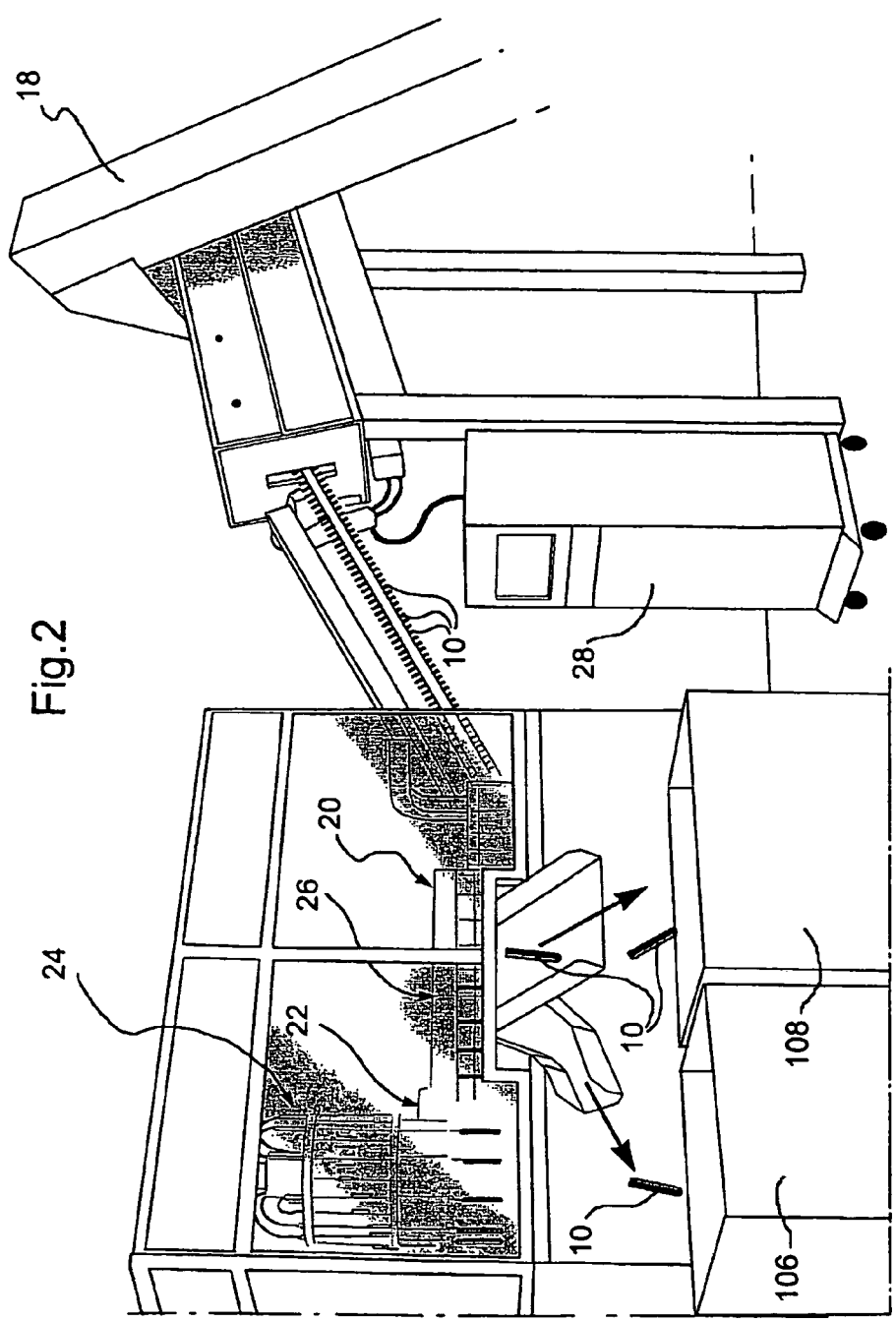
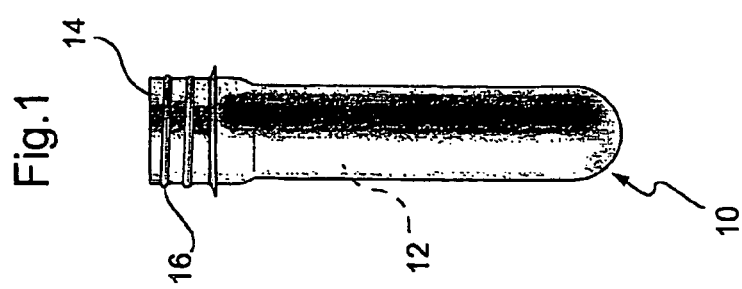

APPARATUS FOR CHECKING THE QUALITY OF PREFORMS EACH HAVING A BODY MADE OF PLASTICS MATERIAL

The present invention relates to apparatus for checking the quality of preforms each having a body made of plastics material having an internal cavity communicating with the exterior through an end opening of the body.

These preforms are usually produced by injection moulding and are intended subsequently to be subjected to blowing in order to adopt the desired final shape. A typical example of articles produced by these techniques is that of containers, in particular bottles, made of PET and having capacities which may vary from a few decilitres to several litres.

The object of the present invention is to provide an apparatus which can perform quality checking on these preforms with great reliability and at high speed.

According to the invention, this object is achieved by means of apparatus and a corresponding method of operation which have the characteristics referred to specifically in the appended claims.

By virtue of the presence of both optical and pneumatic checking means, the apparatus of the invention can ascertain the presence of defects of substantially all of the types which usually occur in preforms, such as incorrect dimensions, ovalization, lack of material, minute holes and/or flash at the injection point, annular burns, annular traces of moisture, non-fused spots, crystalline spots, the presence of foreign particles and/or bubbles, and colour variations and streaks.

The use of the apparatus of the invention consequently prevents all of the problems that are brought about by the presence of one or more of the above-mentioned defects during subsequent processing stages as well as during the handling and use of the finished product. In particular, emergency stoppages of the blowing and filling machines, precautionary rejects by these machines, and the production of aesthetically and/or functionally unsatisfactory finished articles, are prevented.

Figure 3:
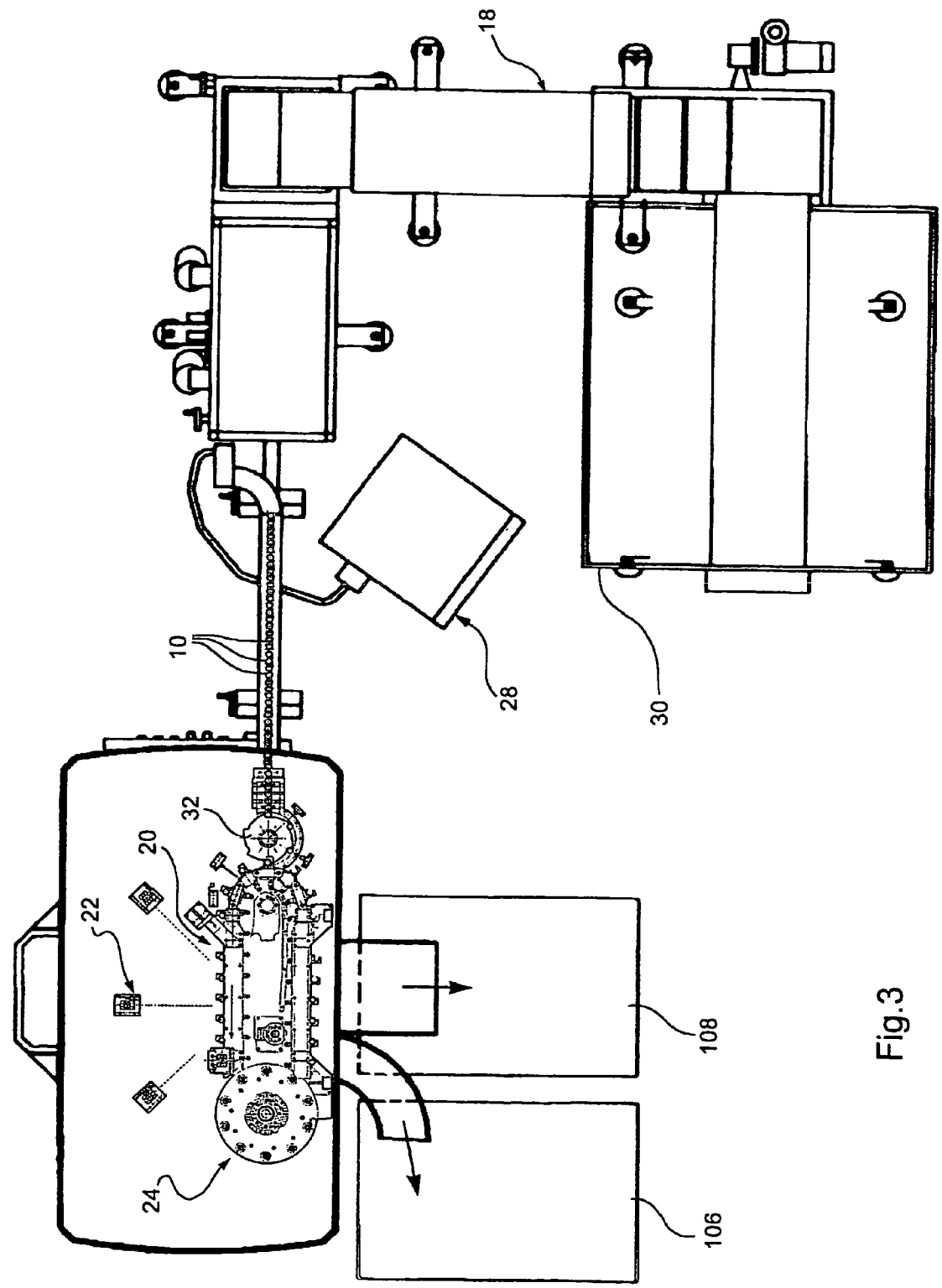
Figure 4:
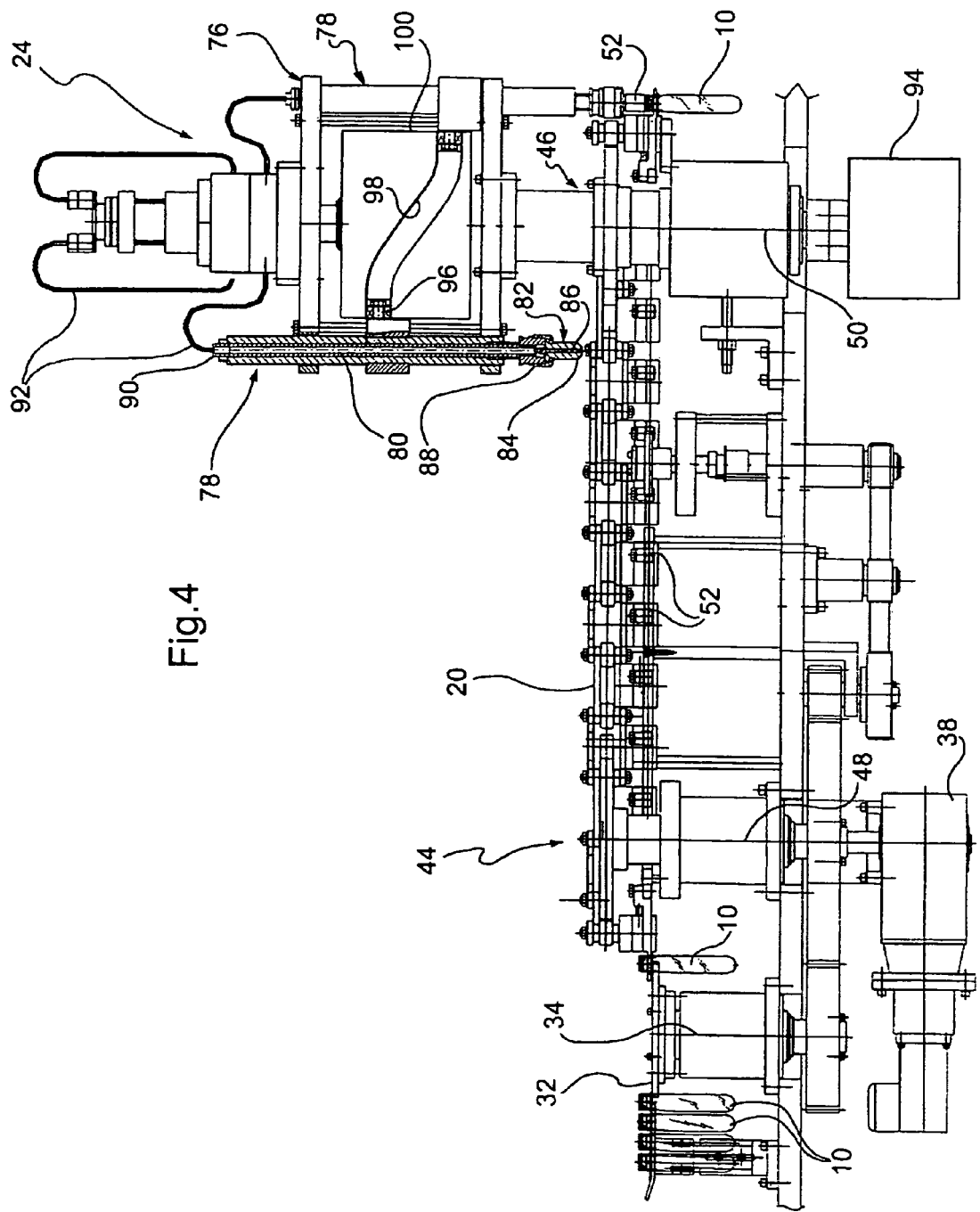
Figure 5:
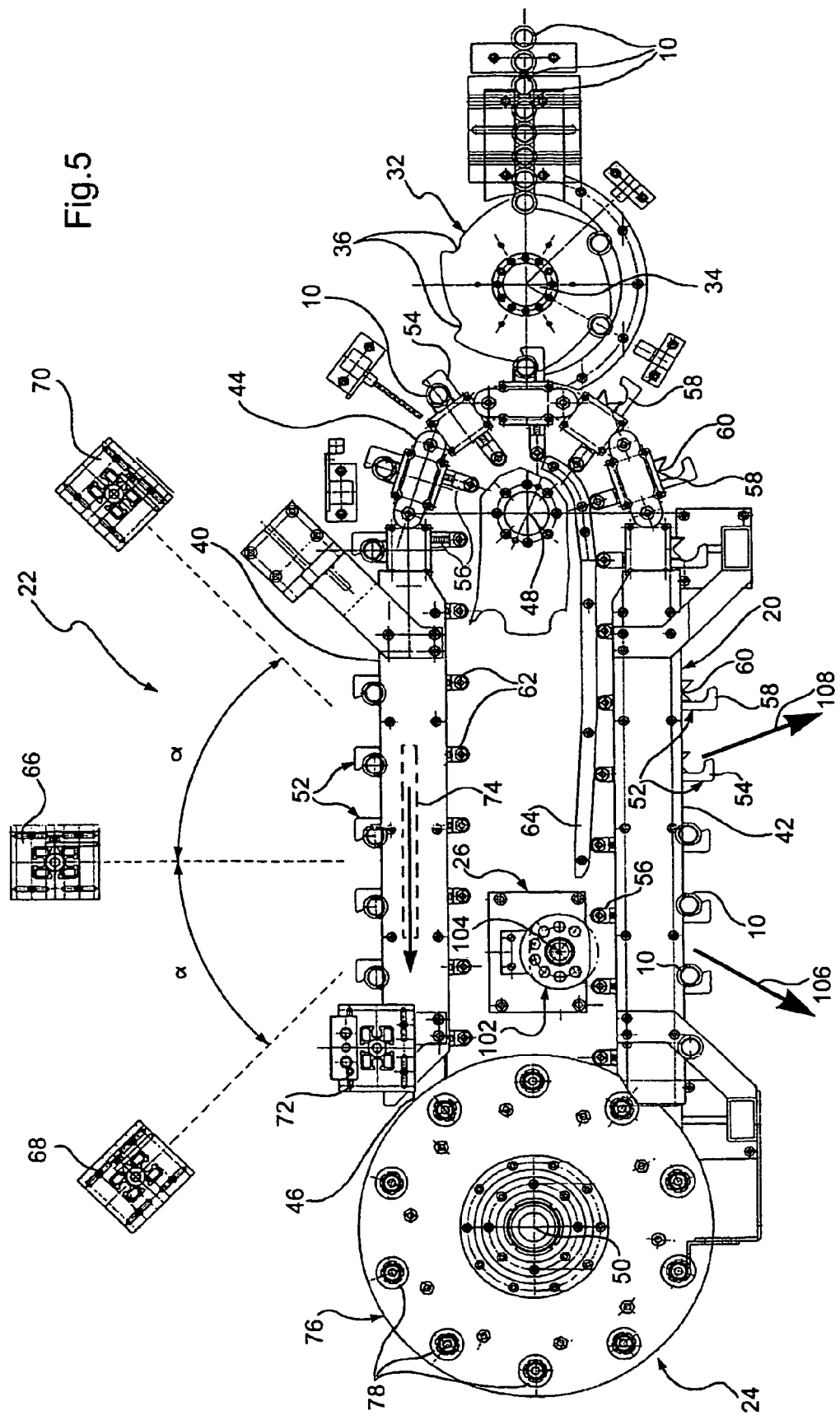

Further advantages and characteristics of the present invention will become clear from the following detailed description which is provided by way of non-limiting example with reference to the appended drawings, in which:

FIG. 1 is an elevational view of a preform which can be checked by the apparatus of the invention, FIG. 2 is an overall perspective view of the apparatus of the invention, FIG. 3 is a schematic plan view of the apparatus of the invention, FIG. 4 is a side elevational view showing some components of the apparatus of the invention, on an enlarged scale, and FIG. 5 is a plan view showing some components of the apparatus of the invention, on an enlarged scale.

The apparatus shown in FIGS. 2 to 5 can be used to perform quality checks on preforms 10 each having (FIG. 1) an oblong body made of plastics material, typically PET. The body has an internal cavity 12 communicating with the exterior through an end opening 14 which is surrounded by an annular collar 16 that projects from the outer surface of the body.

The apparatus comprises (FIGS. 2 and 3) a feed unit 18 for supplying the preforms 10, a conveyor device 20 for transporting them along a predetermined path, an optical device 22, a pneumatic device 24, and a selector device 26 which are arranged along the path, and an electronic control unit 28 suitable for receiving signals from the optical and pneumatic devices 22, 24, processing the signals, and consequently controlling the selector device 26.

The feed unit 18 is of conventional type and enables the preforms 10, which are initially piled up loosely in a container 30, to be arranged in a continuous row in which they are arranged vertically with their open ends 14 facing upwards.

Downstream of the feed unit 18 there is (FIGS. 4 and 5) an input member 32 for introducing the preforms 10 into the conveyor device 20. The input member 32 is constructed in the form of a disc mounted for rotating about its own central axis 34 which is oriented vertically. The disc has on its periphery a plurality of spaced-apart seats 36 suitable for supporting the collars 16 of respective preforms 10.

The conveyor device 20 is of the chain type, extends in an endless circuit in a horizontal plane, and has a drive motor 38. It has an outward pass 40, a return pass 42, and a first end 44 and a second end 46 at which the movement of the chain is reversed about respective axes 48, So which are arranged vertically.

The conveyor device 20 further comprises a plurality of members 52 for the selective gripping of respective preforms 10. Each member 52 comprises a bar 54 which is arranged horizontally and is mounted so as to be movable along an axis substantially perpendicular to the axis of movement of the chain and which has resilient biasing means, in particular a helical spring 56. Each bar 54 has a shaped gripping end 58 which can clamp a preform 10 against a recessed seat 60 formed in the chain, and an opposite end 62 which acts as a follower and can interfere with a control member 64 which is arranged internally beside the end portion of the return pass 42 and the initial portion of the first end 44 of the conveyor device 20. The plane in which the bars 54 of the gripping members 52 lie is disposed at a level slightly above that of the general plane of the disc of the input member 32.

The optical device 22 comprises a plurality of television cameras 66, 68, 70, 72 and means 74 for illuminating the preforms 10, for example, one or more incandescent or fluorescent lamps arranged in the region of the outward pass 40 of the conveyor device 20. The first television camera 66 is arranged beside the path so that its optical axis intersects the path substantially perpendicularly. The second and third television cameras 68, 70 are arranged on opposite sides of the first television camera 66 so that their respective optical axes are inclined at respective acute angles α, for example, of the order of 45°, to the optical axis of the first television camera 66. Finally, the fourth television camera 72 is disposed above the path defined by the conveyor device 20.

The pneumatic device 24 comprises a carousel 76 mounted for rotating about its central axis 50 which is arranged vertically and coincides with that of the second reversal end 46 of the conveyor device 20. The carousel 76 supports on its periphery a plurality of tubular rods 78 mounted so as to be movable along axes parallel to the axis 50. Each rod 78 has a longitudinal internal cavity 80 and a lower end provided with a closure element 82 with a protuberance 84 with a rounded head having a through-hole 86 which is connected to the cavity 78 and with which a pressure sensor 88 is associated. Each rod 78 also has an open upper end 90 which is connected by means of pipes 92 to suction means 94, such as, for example a suction pump. A pin 96 projects radially inwardly from the lateral surface of each rod 78 and extends into a corresponding groove 98 formed on the outer surface of a stationary cylindrical body 100 mounted coaxially around the axis 50 of the carousel 76.

The selector device 26 is disposed along the return pass 42 of the conveyor device 20, upstream of the control member 64. It comprises a cam 102 mounted for rotating about a vertical axis 104 and having sectors of different radial extent so that it can interfere selectively with the follower ends 62 of the bars 54 of the gripping members 54, according to its own angular positioning relative to the axis 104.

The apparatus described above operates as follows.

Each preform 10 supplied by the unit 18 is received individually in a seat 36 of the disc of the member 32 and is brought to the region of the first end 44 of the conveyor device 20 as a result of the rotation of the disc about its own axis 34. The gripping ends 58 of the bars 54 approach the disc in an extended configuration as a result of the interference which is created between the follower ends 62 and the control member 64 and each gripping end 58 can thus encompass the neck of a respective preform 10 between its own internal surface and the seat 60 of the chain facing that surface. As soon as the follower end 62 of the bar 54 of a given gripping member 52 is no longer in contact with the control member 64 as a result of the movement of the conveyor device 20, the spring 56 brings about retraction of the gripping end 58 which thus clamps the preform 10 against the associated seat 60. The preform 10 is thus loaded onto the conveyor device 20 and is carried towards the optical device 22 by virtue of the movement of the conveyor.

The three television cameras 66, 68, 70, which frame each preform 10 successively as it passes along the outward pass 40, can provide a substantially complete image of the lateral surface of the preform 10, and the fourth television camera 72 can provide a plan view thereof.

These images are transmitted to the control unit 28 and are compared with a previously stored reference image of a standard preform. This comparison is performed with the use of conventional software programmes and enables an assessment to be made as to whether or not a given preform 10 satisfies the required quality standards. In particular, the presence of any abrupt spatial variations in the light reflection and/or transmission levels, which indicate the presence of defects, is checked. In accordance with this assessment, the control unit 28 issues a command which is executed at the moment at which the preform 10 passes the selector device 26. If desired, the control unit 28 can also emit warning signals, for example, optical and/or acoustic signals, when the presence of a defect is indicated.

The preform 10 which has been examined by the optical device 22 is then sent towards the pneumatic device 24 which is disposed in the region of the second end 46 of the conveyor device 20. Here, the rotation of the carousel 76 brings about lowering of the rods 78, owing to the engagement of the pins 96 in a downwardly inclined portion of the corresponding groove 98, so that the round-headed protuberances 84 which close their lower ends enter the open upper ends 14 of respective preforms 10.

When the lowering movement of a rod 78 has been completed and the protuberance 84 is inserted in the open end 14 of the preform 10 in a leaktight manner, the suction means 94 are activated and produce a desired degree of vacuum in the cavity 12 of the preform 10 through the pipes 92, the tubular cavity 80, and the hole 86. If the preform is free of defects, it remains under vacuum for the time taken by the preform 10 and by the rod 78 associated therewith to rotate about the axis 50 until the pin 96 is engaged in an upwardly inclined portion of the groove 98 and causes the rod 78 to be lifted and the protuberance 84 to be disengaged from the open end 14 of the preform 10. During this period of time, the sensor 88 measures the value of the pressure prevailing in the cavity 12 and transmits it to the control unit 28 which checks whether the vacuum value initially imposed has remained substantially unchanged. In this case again, on the basis of the outcome of this check, the control unit 28 issues a command which will be executed at the moment when the preform 10 passes the selector device 26.

In detail, if at least one of this latter check and the comparison previously performed between the image of the preform 10 produced by the television cameras 66, 68, 70, 72 and a standard reference image has given a negative result, the control unit 28 brings about a rotation of the cam 102 about its own axis 104 which causes it to interfere with the follower end 62 of the gripping member 52 which engages the preform 10 in question. The gripping end 58 of the bar 54 is thus moved away from the associated seat 60, with consequent disengagement of the preform 10 which falls into a first, reject-collection container 106. In this connection, it should be noted that, if a particular preform 10 has not passed the optical assessment, it is not necessary to place it under partial vacuum when it passes through the pneumatic device 24, since its rejection has already been decided upon.

If, however, the preform 10 has positively passed both the pneumatic check and the optical comparison, the control unit 28 does not bring about a rotation of the cam 102. The movement of the gripping end 58 of the bar 54 away from the associated seat 60 therefore takes place only when the follower end 62 interferes with the initial portion of the control member 64 which is disposed beside the end portion of the return pass 42 of the conveyor device 20. In this case, therefore, the preform 10 falls into a second collecting container 108 and is destined for subsequent blowing in order to adopt the desired final shape.

The apparatus described can check as many as 22,000 preforms per hour, irrespective of their type and size, and can detect defects of dimensions even less than 0.35 mm when examining a region of 150 mm.

Naturally, the principle of the invention remaining the same, the details of construction and forms of embodiment may vary widely with respect to those described purely by way of example, without thereby departing from its scope. In particular, the apparatus of the invention could also be mounted immediately downstream of a preform injection-moulding plant and could be supplied directly with the preforms just moulded. In this case, the prompt detection of any repeating defects could enable the moulding parameters to be modified in good time, thus limiting the number of preforms to be rejected.

Moreover, the arrangement of the optical and pneumatic devices could be the reverse of that shown in the drawings, with consequent reversal of the order in which the respective checks are performed.

The invention claimed is:

1. An apparatus for checking the quality of preforms (10) each having a body made of plastics material having an internal cavity (12) communicating with the exterior through an end opening (14) of the body, the apparatus comprising:

a conveyor device (20) for transporting the preforms (10) along a predetermined path, an optical device (22) disposed along the path and suitable for forming an image of each of the preforms (10), a pneumatic device (24) disposed along the path and suitable for putting the internal cavity (12) of each of the preforms (10) under partial vacuum for a predetermined period of time, an electronic control unit (28) suitable for comparing the images of the preforms (10) with a standard reference image and/or for checking whether the value of the partial vacuum remains unchanged during the said period of time, a selector device (26) disposed along the path and capable of separating the preforms (10) on the basis of the result of the comparison and/or checking operations performed by the control unit (28), a carousel (76) mounted for rotating about its central axis (50) and supporting on its periphery a plurality of tubular rods (78) mounted so as to be movable along axes parallel to the axis (50), each rod (78) having a longitudinal internal cavity (80), a lower end provided with a closure element (82) with a protuberance (84) with a rounded head having a through-hole (86) which is connected to the cavity (80) and with which a pressure sensor (88) is associated, and an upper open end (90) which is connected to suction means (94) and in which a pin (96) projects radially inwardly from the lateral surface of each rod (78) and extends into a corresponding groove (98) formed on the outer surface of a stationary cylindrical body (100) mounted coaxially around the axis (50) of the carousel (76).

2. An apparatus for checking the quality of preforms (10) each having a body made of plastics material having an internal cavity (12) communicating with the exterior through an end opening (14) of the body, the apparatus comprising:

a conveyor device (20) for transporting the preforms (10) along a predetermined path;

an optical device (22) disposed along the path and suitable for forming an image of each of the preforms (10);

a pneumatic device (24) disposed along the path and suitable for putting the internal cavity (12) of each of the preforms (10) under partial vacuum for a predetermined period of time, wherein the pneumatic device (24) comprises a carousel (76) mounted for rotating about its central axis (50) and supporting on its periphery a plurality of tubular rods (78) mounted so as to be movable along axes parallel to the axis (50), each rod (78) having a longitudinal internal cavity (80), a lower end provided with a closure element (82) with a protuberance (84) with a rounded head having a through-hole (86) which is connected to the cavity (80) and with which a pressure sensor (88) is associated, and an upper open end (90) which is connected to suction means (94);

an electronic control unit (28) suitable for comparing the images of the preforms (10) with a standard reference image and/or for checking whether the value of the partial vacuum remains unchanged during the said period of time;

a selector device (26) disposed along the path and capable of separating the preforms (10) on the basis of the result of the comparison and/or checking operations performed by the control unit (28); and in which a pin (96) projects radially inwardly from the lateral surface of each rod (78) and extends into a corresponding groove (98) formed on the outer surface of a stationary cylindrical body (100) mounted coaxially around the axis (50) of the carousel (76).

3. An apparatus for checking the quality of preforms (10) each having a body made of plastics material having an internal cavity (12) communicating with the exterior through an end opening (14) of the body, the apparatus comprising:

a conveyor device (20) for transporting the preforms (10) along a predetermined path, the conveyor device comprising a plurality of members (52) for the selective gripping of a respective preform (10), in which each of the selective gripping members (52) comprises a bar (54) mounted so as to be movable along an axis substantially perpendicular to the axis of movement of the chain and provided with resilient biasing means, the bar (54) having a shaped gripping end (58) which can clamp a preform (10) against a recessed seat (60) formed in the chain and an end (62) which acts as a follower and can interfere with a control member (64) disposed in the region of the end portion of a return pass (42) and of the initial portion of the first end (44) of the conveyor device (20), in which the conveyor device (20) is a chain, extends in an endless circuit in a horizontal plane, has an outward pass (40), a return pass (42), and a first end and a second end (44, 46) at which the movement of the chain is reversed;

an optical device (22) disposed along the path and suitable for forming an image of each of the preforms (10);

a pneumatic device (24) disposed along the path and suitable for putting the internal cavity (12) of each of the preforms (10) under partial vacuum for a predetermined period of time;

an electronic control unit (28) suitable for comparing the images of the preforms (10) with a standard reference image and/or for checking whether the value of the partial vacuum remains unchanged during the said period of time;

a selector device (26) disposed along the path and capable of separating the preforms (10) on the basis of the result of the comparison and/or checking operations performed by the control unit (28).

4. The apparatus according to claim 3 in which the selector device (26) is disposed upstream of the control member (64) and comprises a cam (102) mounted for rotating about a vertical axis (104) and having sectors of different radial extent so that it can interfere selectively with the follower ends (62) of the bars (54) according to its own angular position relative to the axis (104).

* * * * *